(12) United States Patent
Jain et al.

(10) Patent No.: US 9,642,808 B2
(45) Date of Patent: May 9, 2017

(54) EXTENDED RELEASE COMPOSITIONS COMPRISING MYCOPHENOLATE SODIUM AND PROCESSES THEREOF

(75) Inventors: Rajesh Jain, New Delhi (IN); Sukhjeet Singh, New Delhi (IN); Sampath Kumar Devarajan, New Delhi (IN)

(73) Assignee: PANACEA BIOTECH LIMITED, New Delhi (IN)

( * ) Notice: Subject to any disclaimer, the term of this patent is extended or adjusted under 35 U.S.C. 154(b) by 608 days.

(21) Appl. No.: 12/672,180

(22) PCT Filed: Aug. 11, 2008

(86) PCT No.: PCT/IN2008/000505
§ 371 (c)(1),
(2), (4) Date: Feb. 4, 2010

(87) PCT Pub. No.: WO2009/022355
PCT Pub. Date: Feb. 19, 2009

(65) Prior Publication Data
US 2011/0223249 A1    Sep. 15, 2011

(30) Foreign Application Priority Data
Aug. 13, 2007 (IN) .......................... 1714/DEL/2007

(51) Int. Cl.
*A61K 31/343* (2006.01)
*A61K 9/20* (2006.01)
*A61K 9/28* (2006.01)
*A61K 31/365* (2006.01)

(52) U.S. Cl.
CPC .......... *A61K 9/2077* (2013.01); *A61K 9/2013* (2013.01); *A61K 9/2846* (2013.01); *A61K 31/365* (2013.01)

(58) Field of Classification Search
CPC .................................................. A61K 9/2013
USPC ........................................................ 424/465
See application file for complete search history.

(56) References Cited

U.S. PATENT DOCUMENTS 5,334,593 A * 8/1994 Imaizumi et al. ............. 514/274
6,025,391 A    2/2000 Haeberlin et al.

FOREIGN PATENT DOCUMENTS

| WO | 2003/032978 | | 3/2003 | |
| WO | WO 03/032978 | * | 4/2003 | ........... A61K 31/365 |
| WO | 2006/024479 | | 3/2006 | |
| WO | WO2006/024479 | * | 3/2006 | ........... A61K 31/365 |

OTHER PUBLICATIONS

Remington (Remington: The Science and Practice of Pharmacy. 19th edition. p. 1662. (1995)).*
FDA (Guidance for Industry. Bioavailability and Bioequivalence Studies for Orally Administered Drug Products—General Considerations (Oct. 2000)).*

* cited by examiner

*Primary Examiner* — Jake Vu
(74) *Attorney, Agent, or Firm* — Seyfarth Shaw LLP (57) ABSTRACT

Extended release pharmaceutical compositions comprising mycophenolate sodium as the active agent, wherein the said composition exhibits a characteristic release profile when subjected to in-vitro dissolution study, and wherein said mycophenolate sodium is released in a sustained manner in-vivo for a prolonged duration in such quantities that substantially alleviates or at least reduces the chances of causing any associated gastrointestinal side effect(s) without compromising the bioavailability of the said active agent are provided. The present invention also provides process of preparing dosage form compositions and prophylactic and/or therapeutic methods of using such dosage form. The compositions of the present invention are useful for the management such as prophylaxis, amelioration and/or treatment of immunosuppressant indicated disease(s)/disorder(s) especially for the treatment or prevention of organ, tissue or cellular allograft or xenograft rejection, e.g. after transplant, or the management of immune-mediated diseases (autoimmune diseases).

2 Claims, 2 Drawing Sheets

EXTENDED RELEASE COMPOSITIONS COMPRISING MYCOPHENOLATE SODIUM AND PROCESSES THEREOF

FIELD OF THE INVENTION

The present invention relates to extended release pharmaceutical compositions comprising mycophenolate sodium as the active agent, wherein the said composition exhibits a characteristic release profile when subjected to in-vitro dissolution study, and wherein said mycophenolate sodium is released in a sustained manner in-vivo for a prolonged duration in such quantities that substantially alleviates or at least reduces the chances of causing any associated gastrointestinal side effect(s) without compromising the bioavailability of the said active agent. The present invention also provides process of preparing such dosage form compositions and prophylactic and/or therapeutic methods of using such dosage form. The composition of the present invention are safe, effective and well-tolerated, and are useful for the management such as prophylaxis, amelioration and/or treatment of immunosuppressant indicated disease(s)/disorder(s) especially for the treatment or prevention of organ, tissue or cellular allograft or xenograft rejection, e.g. after transplant, or the management of immune-mediated diseases (autoimmune diseases).

BACKGROUND OF THE INVENTION

Many medical conditions are best treated by administration of a pharmaceutical in such a way as to modify its action over an extended period of time. Modified release form means a formulation which releases the drug not immediately, e.g. after disintegration or in case of enteric-coating, i.e. gastro-resistant coating, after stomach passage, but offers a sustained, retard, continuous, gradual, prolonged or pulsatile release and therefore alters drug plasma levels distinctively versus an immediate release formulation.

Mycophenolic acid (MPA) was first isolated in 1896, and has been extensively investigated as a pharmaceutical of potential commercial interest. It is known to have anti-tumor, anti-viral, immunosuppressive, anti-psoriatic, and anti-inflammatory activity [see e.g. W. A. Lee et al, Pharmaceutical Research (1990), 7, p. 161-166 and references cited therein]. A derivative of MPA such as mycophenolate mofetil (MMF) had been introduced commercially in the US and elsewhere under the brand name CellCept® as an immunosuppressant in the immediate release form for the treatment or prevention of organ or tissue transplant rejection. A pharmaceutical delayed release composition comprising mycophenolate sodium (Myfortic®) has been approved for marketing in the United States. It has been concluded in a study that mycophenolate sodium is therapeutically equivalent to MMF at equimolar MPA doses. 769.4 mg of mycophenolate sodium contains equimolar amounts of MPA compared with 1000 mg of MMF [Progress in Transplantation; June 2004; Gabardi, S et al]. Mycophenolate Sodium salts are known, e.g. in South African Patent 68/4959. U.S. Pat. Nos. 6,025,391, 6,172,107 and 6,306,900 describe pharmaceutical compositions comprising a mycophenolate salt, wherein the composition is enteric coated thereby preventing the release of the mycophenolate salt in the stomach, and releasing the mycophenolate salt in the upper part of the intestinal tract. However the major limitation of formulating such a composition of mycophenolate is that although the enteric coat is intended to prevent release of the drug in the stomach to prevent associated side effects, the clinical study results in 423 de novo kidney allograft recipients indicates that the incidence of GI adverse events was 79.8% with mycophenolate sodium and 77.1% with MMF (P=NS) and also the frequency of dosage reductions, discontinuation, or temporary interruptions of therapy secondary to GI toxicities were comparable. It is well known from the literature that Mycophenolate mofetil (MMF) is a prodrug containing mycophenolic acid (MPA) as the active moiety which is an inhibitor of de novo purine nucleotide synthesis. MMF can cause toxicity, mainly of hematologic and/or gastrointestinal nature (Transplantation, Van Gelder et al., 1999). It has been reported that occurrence of side effects due to MMF is the major reason for reducing the dose of MMF which leads to graft loss. Enteric coated mycophenolate sodium (EC-MPS), the advanced enteric-coated formulation of MPA is the salt mycophenolate sodium, has a delayed release because of the enteric coating and is released in the small intestine. This enteric coated formulation, apart from the above-mentioned issues, is expected to result in an improper and incomplete absorption and/or undesired absorption pattern of the drug that may be achieved since the drug is not getting absorbed from the entire gastro-intestinal tract (GIT), but instead restricted to absorption from only the intestinal region. Table 1 enlists the adverse effects of MMF and EC-MPS in controlled de novo and maintenance renal transplantation studies. There seems to be no significant difference in the side effects on post administration of both, MMF and EC-MPS.

TABLE 1

Adverse Events (%) in Controlled de novo and Maintenance Renal Studies Reported in 20% of Patients

| Side effects | MMF (%) | MPS (%) |
|---|---|---|
| Blood and Lymphatic System disorder | | |
| Anemia | 21.6 | 21.9 |
| Leukopenia | 19.2 | 20.5 |
| Gastrointestinal System Disorders | | |
| Constipation | 38.0 | 39.5 |
| Nausea | 29.1 | 27.1 |
| Diarrhoea | 24.8 | 23.5 |
| Vomiting | 20 | 23 |
| Dyspepsia | 22.5 | 19 |
| Infections and infestations | | |
| Urinary Tract Infection | 29.1 | 33.3 |
| CMV infections | 20.2 | 18.1 |
| Nervous System Disorders | | |
| Insomnia | 23.5 | 23.8 |

The etiology of the observed gastrointestinal effects due to MMF was reviewed by Behrend et al (Adverse Gastrointestinal Effects of Mycophenolate Mofetil Aetiology, Incidence and Management, 2001). It was concluded by the authors that the gastrointestinal adverse effects of MMF were mainly related to $C_{max}$ of the active moiety i.e., MPA whereas the efficacy was related to AUC. A few other authors have also reported that there is a correlation between plasma concentration of MPA (C30) and side effects (Correlation of mycophenolic acid pharmacokinetic parameters with side effects in kidney transplant patients treated with mycophenolate mofetil, Clinical Chemistry, 2001, Mourad et al).

The insignificant difference in the adverse effects of MMF and EC-MPS (Table 1) can be attributed to high $C_{max}$ value of MPA in both the cases. The values of $C_{max}$ for MMF (1 g b.i.d) and EC-MPS (720 mg b.i.d) were found to be 21.3 and 18.93 µg/mL respectively (Am J Transplant, 2007, Budde et al.). Hence, there still exists an unmet need for developing a suitable dosage form which releases the drug mycophenolate sodium throughout the GIT in a sustained release manner to achieve the desired $C_{max}$ with optimum AUC for achieving better patient compliance as extended release dosage form of MPS will have lower $C_{max}$ as compared to MMF or EC-MPS and may lead to reduction in side effects.

PCT Publication No. WO2006024479 discloses a composition comprising mycophenolic acid, a salt or a prodrug thereof in a modified release form. Such compositions are intended to improve the drug distribution in the intestine, and to delay the delivery of the drug substance to the intestinal tract. Multiparticulate systems such as granules, pellets, beads and minitablets are disclosed. Also disclosed are coated pellets and granules compressed into rapid disintegrating tablets. However no single unit dosage forms either uncoated or coated for providing a sustained release of mycophenolate sodium particularly throughout the GIT are disclosed. Further the multiparticulate system of the said publication if formulated as a compressed dosage form such as tablet, the application of compression force in a compression machine will lead to rupturing of the coated multiple units resulting in loss of uniformity of the coating layer over the entire unit (pellet or granule) thus producing variable and unpredictable release of the active agent from such compressed forms. Furthermore the multiparticulate system of the present invention lacks patient compliance since the multiple units such as pellets or granules if administered orally to a patient will cause an unpleasant and gritty feeling in the mouth and would be difficult to swallow since it might stick to the oral cavity. Still further, such multiparticulate systems would require the use of an additional taste-masking agent in the composition.

PCT Publication No. WO2005034916 describes a composition comprising mycophenolic acid, a salt or a prodrug thereof in multiparticulate form such that the compositions disintegrate or dissolve in the mouth, stomach or small intestine to give multiparticles, wherein the multiparticles are enteric coated. Such compositions do not provide a uniform sustained release of the active agent throughout the GIT; instead it releases the drug only in the intestine. Further the drug release from the multiparticulate systems are generally non-uniform since it is extremely difficult to predetermine and/or control the behavior of such systems upon in vivo administration.

US Publication No. 20060280795 discloses an enteric coated delivery device for the delayed release of an active agent in the gastrointestinal tract comprising a core comprising an active agent; a first outer coating, comprising a relatively hydrophobic substantially water insoluble polymer having substantially water insoluble hydrophilic particles embedded therein; and a first inner coating layer, comprising an agent that can cause the dissolution of at least one of said water insoluble components of said outer coating, and optionally a water soluble polymer, such that said insoluble particles in said outer coating, upon absorption of liquid, form channels leading to said inner coating layer, thus enabling the dissolution thereof, whereby the agents contained therein are released to cause at least the dissolution, degradation or destruction of said outer coating, and the release of the active agent from the core of said device. Such compositions do not provide a sustained release of the active agent throughout the GIT; instead it releases the drug only in the intestine.

U.S. Pat. No. 5,554,384 discloses high dose pharmaceutical formulation preferably as a capsule comprising a therapeutically effective amount of an active agent selected from the group consisting of mycophenolate mofetil and mycophenolic acid, said active agent having been heated to a first temperature above its melting point, cooled to a second temperature below its melting point at which second temperature said active agent remained liquefied, and filled into a pharmaceutical dosage form while in said cooled liquefied state. However the said patent does not disclose any sustained release composition comprising mycophenolate mofetil and mycophenolic acid; neither does it disclose any compositions comprising a substantially high dose of mycophenolate sodium.

A review of the prior art literature shows that no formulation has been approved till date for a sustained release pharmaceutical composition comprising mycophenolate sodium. Mycophenolate sodium formulations disclosed in prior art are particularly multiparticulate and/or enteric-coated (delayed release) systems which suffer from several disadvantages as discussed earlier. Hence there still exists a need for commercially acceptable preferably single unit dosage forms for oral administration with good patient convenience and acceptance. Also there is still an unmet need to develop especially once-a-day mycophenolate compositions comprising substantially high dose of said active agent for sustained release particularly from a matrix system such that the inter- and intra-patient variability is reduced. Particularly there still exists a need for developing oral mycophenolate sodium compositions which are stable and easily swallowable upon oral administration, possess appreciable bioavailability characteristics, are well-tolerated and safe, and exhibit a drug release for a substantially longer duration. Also there exists a need to develop oral pharmaceutical compositions comprising mycophenolate sodium for prophylactic and/or therapeutic use, which can release the drug in a desired manner such as to maintain therapeutic levels of the drug in the plasma for extended period of time but without causing drug related toxicity, and which can be prepared in an easy and cost-effective manner.

The inventors of the present invention have done extensive research and conducted several experiments to alleviate the drawbacks existing in the prior art to develop dosage form compositions comprising mycophenolate sodium by using different excipients and formulation methods for preferably modifying the release rate of said immunosuppressant so as to obtain the desired in-vitro release characteristics which aids in the interpretation of predictable behavior of the dosage form in-vivo as mentioned earlier. The compositions of the present invention are preferably unit dosage forms which provides prophylactic and/or therapeutic concentration of the active agent for an extended duration of time devoid of any substantial toxicity, thus demonstrating a significant advancement over the prior art. The inventors of the present invention have invented extended release formulations of mycophenolate sodium, characterized in that mycophenolate sodium is released in a sustained manner, alleviating or at least reducing the chances of causing any associated side effects without compromising the bioavailability of active agent. Further, the active agent mycophenolate sodium is well absorbed orally and and/or the variation of its absorbability is substantially alleviated when made into compositions according to the present invention.

SUMMARY OF THE INVENTION

It is an objective of the present invention to provide extended release compositions comprising mycophenolate sodium as the active agent for once-a-day or twice-a-day administration, wherein the said composition exhibits a characteristic release profile when subjected to in-vitro dissolution study which is useful in predicting the in-vivo behavior, and wherein said mycophenolate sodium is released in a sustained manner in-vivo for a prolonged duration in such quantities that substantially alleviates or at least reduces any associated gastrointestinal side effect(s) and/or the inter- and intra-patient variability, without compromising the bioavailability of the said active agent.

It is an objective of the present invention to provide extended release compositions comprising mycophenolate sodium as the active agent for once-a-day or twice-a-day administration, wherein the said composition provides a better patient compliance by reducing the frequency of dosage form administration and also resulting in lesser episodes of allograft or xenograft transplant rejections.

It is another objective of the present invention to provide extended release composition comprising mycophenolate sodium as active agent, wherein the time (T50%) required for 50% of the maximum amount of mycophenolate sodium to be dissolved is 0.5 to 16 hours, when the composition is subjected to an in-vitro dissolution test using USP Apparatus-I (Basket method, 100 rpm) and using pH 6.8 phosphate buffer as dissolution medium maintained at about 37±0.5° C.

It is another objective of the present invention to provide extended release composition comprising mycophenolate sodium as active agent, at least one release controlling material(s), optionally alongwith one or more pharmaceutically acceptable excipient(s), wherein not more than about 50% w/w of the active agent is released within 2 hours, when the composition is subjected to an in-vitro dissolution test using USP Apparatus-I (Basket method, 100 rpm) and using 0.1 N HCl as dissolution medium maintained at about 37±0.5° C.

It is another objective of the present invention to provide extended release composition comprising mycophenolate sodium as active agent, at least one release controlling material(s), optionally alongwith one or more pharmaceutically acceptable excipient(s), wherein the said release controlling material(s) is hydrophilic or hydrophobic or amphiphilic in nature or mixtures thereof, and wherein not more than about 50% w/w of the active agent is released within 2 hours, when the composition is subjected to an in-vitro dissolution test using USP Apparatus-I (Basket method, 100 rpm) and using 0.1 N HCl as dissolution medium maintained at about 37±0.5° C.

It is another objective of the present invention to provide extended release composition comprising mycophenolate sodium as active agent, at least one release controlling material(s), optionally alongwith one or more pharmaceutically acceptable excipient(s), wherein not more than about 50% w/w of the active agent is released within 2 hours, when the composition is subjected to an in-vitro dissolution test using USP Apparatus-II (Paddle method, 100 rpm) and using 0.1 N HCl as dissolution medium maintained at about 37±0.5° C.

It is another objective of the present invention to provide extended release composition comprising mycophenolate sodium as active agent, at least one release controlling material(s), optionally alongwith one or more pharmaceutically acceptable excipient(s), wherein the said release controlling material(s) is hydrophilic or hydrophobic or amphiphilic in nature or mixtures thereof, and wherein not more than about 50% w/w of the active agent is released within 2 hours, when the composition is subjected to an in-vitro dissolution test using USP Apparatus-II (Paddle method, 100 rpm) and using 0.1 N HCl as dissolution medium maintained at about 37±0.5° C.

It is also an objective of the present invention to provide novel extended release compositions comprising mycophenolate sodium as the active agent particularly in the form of solid oral dosage forms, wherein the said dosage forms exhibit a sustained release of the active agent throughout the gastro-intestinal tract such that a sufficient amount of the active agent is released in the lower part and/or proximal part of the gastro-intestinal tract so as to reduce the drug related gastrointestinal side effects without compromising the systemic bioavailability of the active agent.

It is also an objective of the present invention to provide extended release composition comprising mycophenolate sodium as active agent, wherein at least about 10% of the active agent is released within 4 hours, when subjected to an in-vitro dissolution test using USP Apparatus-I (Basket method, 100 rpm) and using 0.1 N HCl as dissolution medium during the first 2 hours followed by a dissolution medium having a pH of 6.8 thereafter maintained at about 37±0.5° C.

It is also an objective of the present invention to provide extended release compositions comprising mycophenolate sodium as active agent, wherein at least about 10% of the active agent is released within 4 hours, when subjected to an in-vitro dissolution test using USP Apparatus-II (Paddle method, 100 rpm) and using 0.1 N HCl as dissolution medium maintained at about 37±0.5° C. during the first 2 hours followed by a dissolution medium having a pH of 6.8 thereafter maintained at about 37±0.5° C.

It is also an objective of the present invention to provide extended release composition comprising mycophenolate sodium as active agent, wherein not more than about 50% w/w of the active agent is released within 2 hours, when subjected to an in-vitro dissolution test using USP Apparatus-I (Basket method, 100 rpm) and using 0.1 N HCl as dissolution medium; and wherein at least about 15% of the active agent is released within 4 hours, when subjected to an in-vitro dissolution test using USP Apparatus-I (Basket method, 100 rpm) and using Distilled water as dissolution medium maintained at about 37±0.5° C.

It is also an objective of the present invention td provide extended release composition comprising mycophenolate sodium as active agent, wherein not more than about 50% w/w of the active agent is released within 2 hours, when subjected to an in-vitro dissolution test using USP Apparatus-II (Paddle method, 100 rpm) and using 0.1 N HCl as dissolution medium; and wherein at least about 15% of the active agent is released within 4 hours, when subjected to an in-vitro dissolution test using USP Apparatus-II (Paddle method, 100 rpm) and using Distilled water as dissolution medium maintained at about 37±0.5° C.

It is also an objective of the present invention to provide extended release composition comprising mycophenolate sodium as active agent, wherein not more than about 50% w/w of the active agent is released within 2 hours, when subjected to an in-vitro dissolution test using USP Apparatus-II (Paddle method, 100 rpm) and using 0.1 N HCl as dissolution medium; and wherein at least about 15% of the active agent is released within 4 hours, when subjected to an in-vitro dissolution test using USP Apparatus-II (Paddle method, 100 rpm) and using Distilled water as dissolution medium maintained at about 37±0.5° C.

It is another objective to provide process of preparation of the composition of the present invention which comprises treating the active agent mycophenolate sodium alongwith at least one release controlling material(s), optionally alongwith one or more pharmaceutically acceptable excipient(s), and formulating into a suitable dosage form.

It is yet another objective of the present invention to provide use of the present pharmaceutical composition in reducing the variability in absorption of mycophenolate sodium throughout the gastro-intestinal tract by providing a substantially uniform sustained release in-vivo and also reducing the chances of causing any associated gastrointestinal side effects, without compromising the bioavailability of the said active agent.

It is yet another objective to provide method of using the composition of the present invention for the management such as prophylaxis, amelioration and/or treatment of immunosuppressant indicated disease(s)/disorder(s) especially for the treatment and/or prevention of organ, tissue or cellular allograft or xenograft rejection, e.g. after transplant, or the management of immune-mediated diseases (autoimmune diseases), which comprises administering to a subject in need thereof the composition comprising a pharmaceutically effective amount of mycophenolate sodium as the active agent.

It is yet another objective of the present invention to provide use of, the pharmaceutical composition comprising pharmaceutically effective amount of mycophenolate sodium in the preparation of a medicament for the management such as prophylaxis, amelioration and/or treatment of immunosuppressant indicated disease(s)/disorder(s) especially for organ, tissue or cellular allograft or xenograft rejection, such as after transplant, or the management of immune-mediated diseases (autoimmune diseases).

The pharmaceutical compositions of the present invention are intended for once-a-day or twice-a-day administration, preferably for once-a-day administration. The once-a-day composition releases the active agent mycophenolate sodium in a desired manner so as to maintain prophylactic and/or therapeutic levels of the active agent in the plasma for extended period of time devoid of any substantial drug related toxicity, and also can be prepared in an easy and cost-effective manner.

DETAILED DESCRIPTION OF THE INVENTION

The present invention provides extended release compositions comprising mycophenolate sodium as the active agent for once-a-day or twice-a-day administration, wherein the said composition provides a better patient compliance by reducing the frequency of dosage form administration and also resulting in lesser episodes of allograft or xenograft transplant rejections. The extended release compositions of the present invention exhibit a characteristic release profile when subjected to in-vitro dissolution study which is useful in predicting the in-vivo behavior. The compositions release the active agent mycophenolate sodium in a sustained manner in-vivo for a prolonged duration in such quantities that substantially alleviates or at least reduces any associated gastrointestinal side effect(s) and/or the inter- and intrapatient variability, without compromising the bioavailability of the said active agent.

The development of an extended release dosage form for mycophenolate sodium is challenging due to the pH-dependent solubility of the drug i.e. high solubility of the drug in pH above 6.0 and poor solubility in pH below 6.0. Furthermore, it is challenging to develop extended release dosage forms of mycophenolate sodium which are robust, and whose dissolution behavior does not depend on the state of digestion or dosage form transit through the gastrointestinal tract. The inventors of the present invention have been able to develop extended release compositions comprising mycophenolate sodium thus demonstrating a significant advancement over the prior art. The present invention provides a stable extended release single unit dosage form composition such as matrix tablets which could provide substantially linear drug release for a prolonged duration of time during the transit through varying pHs of the GIT.

Further, the drug mycophenolate sodium possesses very poor flow properties, poor compressibility and also develops static charges while processing which makes the formulation of a dosage form all the more challenging. Also since mycophenolate sodium is administered in high dose, developing extended release unit dosage forms such as tablet formulations for mycophenolate sodium is very challenging and requires extensive research and experimentation. The present invention provides easy, convenient and reproducible method to manufacture particularly single unit extended release dosage forms comprising mycophenolate sodium. The dosage form composition of the present invention is designed in such a manner that it will not restrict the drug release to certain GIT pHs; instead it will facilitate release of drug through different pHs, which is essential for a desirable extended release dosage form.

The present invention provides extended release compositions comprising mycophenolate sodium as active agent suitable for use in situations where a sustained effect of said active agent for a prolonged duration is desirable in order to develop compositions suitable for administration less frequently such as once or twice daily. Optionally the compositions are also capable of providing an initial rapid effect followed by a sustained effect of the active agent for use in certain situations where such combined effect is desirable.

Mycophenolate sodium and its active metabolite mycophenolic acid are active agents having substantially low solubility in an acidic medium having a pH of from about 1 to about 3, i.e. a pH corresponding to the pH in the stomach. The prior art formulation approaches lead to a pharmaceutical composition which has a suitable fast disintegration time but not necessarily a suitable dissolution rate of the active agent under acidic conditions, i.e. a multiparticulate composition in the form of a tablet with an extragranularly added disintegrant will rapidly disintegrate into granules but the dissolution of the drug substance from the composition and/or the disintegrated composition under acidic conditions may be unsuitable and, low due to the solubility properties of the active agent itself. The availability of an active agent with respect to absorption, i.e. entrance into the circulatory system, is dependant on the presence of the active agent in dissolved form as it is generally accepted that only dissolved substances are capable of passing the mucous membranes in the gastro-intestinal tract. Therefore, it is important that the dissolution of the active agent is suitably fast even under acidic conditions in order to enable absorption from the stomach so that the absorption of the active agent is continuous throughout the GIT, and the bioavailability is not compromised. However, the various approaches disclosed in the prior art with respect to achievement of a suitable extended release profile of mycophenolate sodium in-vivo (e.g. in the patents/publications discussed hereinbefore) do not seem to take the above-mentioned factors into account and, hence, there is still a need for developing compositions which enable a proper extended release of mycophenolate sodium.

The extended release compositions of the present invention are safe, predictable and reliable, and are also very storage stable because an immediate release due to accidental damaging of e.g. the coating or capsule may result in undesired high plasma concentrations, so-called dose dumping, which could cause undesired side effects. Furthermore, the storage stability of the extended release compositions of the present invention is very beneficial from a technical point of view since even a minor change in the release rate and/or release pattern may have a significant impact on the in-vivo performance of the composition. Still further the extended release pharmaceutical composition has been disclosed which at the same time can be produced in an easy, cheap and reliable manner and which provides a suitable profile for release of active agent (under acidic, neutral and basic conditions) resulting in an extended period of about 12 to 24 hours.

The present invention provides extended release compositions comprising mycophenolate sodium as the active agent, wherein the said composition exhibits a characteristic release profile when subjected to in-vitro dissolution study, and wherein said mycophenolate sodium is released in a sustained manner in-vivo for a prolonged duration in such quantities that substantially alleviates or at least reduces the chances of causing any associated gastrointestinal side effect(s) without compromising the bioavailability of said active agent. Preferably the dissolution method employed to test the drug release profile of the composition of the present invention includes a change in pH from acidic to alkaline to simulate the in-vivo situation. In an embodiment, the active agent of the present invention is mycophenolate sodium, e.g. mono or di-sodium salt, preferably mono-sodium salt.

In an embodiment, the present invention provides extended release composition comprising mycophenolate sodium as active agent, wherein the time (T50%) required for 50% of the maximum amount of mycophenolate sodium to be dissolved is 0.5 to 16 hours, when the composition is subjected to an in-vitro dissolution test using USP Apparatus-I (Basket method, 100 rpm) and using pH 6.8 phosphate buffer as dissolution medium maintained at about 37±0.5° C.

In another embodiment, the present invention provides extended release composition comprising mycophenolate sodium as active agent, at least one release controlling material(s), optionally alongwith one or more pharmaceutically acceptable excipient(s), wherein not more than about 50% w/w of the active agent is released within 2 hours, when the composition is subjected to an in-vitro dissolution test using USP Apparatus-I (Basket method, 100 rpm) and using preferably 900 ml of 0.1N HCl as dissolution medium maintained at about 37±0.5° C. It might be appreciated that the dissolution test apparatus used to conduct in-vitro dissolution tests according to the present invention may be USP Apparatus-I (Basket method) or USP Apparatus-II (Paddle method) at 25-125 rpm using a suitable type and volume of the dissolution medium; wherein the volume of the medium is preferably about 400 ml to about 1000 ml. Similarly the compositions when tested by USP Apparatus Type-III (reciprocating cylinder apparatus) at a standard dip rate of 10 dpm (dips per minute) wherein the vessels are filled with about 200 to about 300 ml of 0.1 N HCl as dissolution medium maintained at about 37±0.5° C. and the mesh size of the top and bottom screens are fixed at 420 μm, not more than about 50% w/w of the active agent is released within 2 hours. Measuring the percentage of active agent dissolved can be done by spectroscopic techniques, as well as other well know techniques in the art.

In another embodiment of the present invention is provided extended release compositions comprising mycophenolate sodium as active agent, at least one release controlling material(s), optionally alongwith one or more pharmaceutically acceptable excipient(s), wherein the said release controlling material(s) is hydrophilic or hydrophobic or amphiphilic in nature or mixtures thereof, and wherein not more than about 50% w/w of the active agent is released within 2 hours, when the composition is subjected to an in-vitro dissolution test using USP Apparatus-I (Basket method, 100 rpm) and using 0.1 N HCl as dissolution medium maintained at about 37±0.5° C.

In another embodiment of the present invention is provided extended release compositions comprising mycophenolate sodium as active agent, at least one release controlling material(s), optionally alongwith one or more pharmaceutically acceptable excipient(s), wherein the said release controlling material(s) is hydrophilic or hydrophobic or amphiphilic in nature or mixtures thereof, and wherein not more than about 50% w/w of the active agent is released within 2 hours, when the composition is subjected to an in-vitro dissolution test using USP Apparatus-II (Paddle method, 100 rpm) and using 0.1 N HCl as dissolution medium maintained at about 37±0.5° C.

In another embodiment, the present invention provides extended release compositions comprising mycophenolate sodium as active agent, wherein at least about 10% of the active agent is released within 4 hours, when subjected to an in-vitro dissolution test using USP Apparatus-I (Basket method, 100 rpm) and using 0.1 N HCl as dissolution medium maintained at about 37±0.5° C. during the first 2 hours followed by a dissolution medium having a pH of 6.8 thereafter maintained at about 37±0.5° C.

In another embodiment, the present invention provides extended release compositions comprising mycophenolate sodium as active agent, wherein at least about 10% of the active agent is released within 4 hours, when subjected to an in-vitro dissolution test using USP Apparatus-II (Paddle method, 100 rpm) and using 0.1 N HCl as dissolution medium maintained at about 37±0.5° C. during the first 2 hours followed by a dissolution medium having a pH of 6.8 thereafter maintained at about 37±0.5° C.

In still another embodiment, the present invention provides extended release compositions comprising mycophenolate sodium as active agent, wherein not more than about 50% w/w of the active agent is released within 2 hours, when subjected to an in-vitro dissolution test using USP Apparatus-I (Basket method, 100 rpm) and using 0.1 N HCl as dissolution medium; and wherein at least about 15% of the active agent is released within 4 hours, when subjected to an in-vitro dissolution test using USP Apparatus-I (Basket method, 100 rpm) and using Distilled water as dissolution medium maintained at about 37±0.5° C.

In still another embodiment, the present invention provides extended release compositions comprising mycophenolate sodium as active agent, wherein not more than about 50% w/w of the active agent is released within 2 hours, when subjected to an in-vitro dissolution test using USP Apparatus-II (Paddle method, 100 rpm) and using 0.1 N HCl as dissolution medium; and wherein at least about 15% of the active agent is released within 4 hours, when subjected to an in-vitro dissolution test using USP Apparatus-II (Paddle method, 100 rpm) and using Distilled water as dissolution medium maintained at about 37±0.5° C.

In an embodiment, the present invention provides extended release compositions comprising mycophenolate sodium as active agent, wherein not more than about 50% w/w of the active agent is released within 2 hours; from about 5% to about 75% of the active agent released after 4 hours; and not less than about 40% of the active agent released after 12 hours when subjected to an in-vitro dissolution test using USP Apparatus-I (Basket method, 100 rpm) and using 0.1 N HCl as dissolution medium during the first 2 hours followed by a dissolution medium having a pH of 6.8 thereafter maintained at about 37±0.5° C.

In an embodiment, the present invention provides dosage form compositions that exhibit one or more superior properties relative to unformulated active agent mycophenolate sodium and/or other compositions known in the prior art which comprise the said active agent. These superior properties include, but are not limited to, one or more of the following: improved bioavailability; improved solubility of the pharmaceutical composition; decreased disintegration times for immediate release oral dosage forms; decreased dissolution times for immediate release oral dosage forms; improved dissolution profiles for controlled release oral dosage forms; decreased tablet friability; increased tablet hardness; reduced toxicity, improved safety for oral dosage forms; reduced moisture content and/or hygroscopicity for oral dosage forms; improved composition wettability; improved particle size distribution of active agent, improved composition compressibility; improved composition flow properties; improved chemical stability of the final oral dosage form; improved physical stability of the final oral dosage form; decreased tablet/capsule size; improved blend uniformity; improved dose uniformity; increased granule density for wet granulated compositions; reduced water requirements for wet granulation; reduced wet granulation time; and/or reduced drying time for wet granulated mixtures.

In yet another embodiment, the present invention provides novel extended release compositions comprising mycophenolate sodium as the active agent particularly as solid oral dosage forms, wherein the said dosage forms exhibit a sustained release of the active agent throughout the gastro-intestinal tract such that only a sufficient amount of the active agent is released in the lower part and/or proximal part of the gastro-intestinal tract so as to reduce the drug related gastrointestinal side effects without compromising the systemic bioavailability of the active agent.

In a further embodiment, the composition of the present invention additionally comprises at least one other active agent(s). The other active agent useful in the present invention may be any agent known to the art that can be administered in combination with an immunosuppressant such as an active agent(s) selected from but not limited to a group comprising cardiovascular drug, respiratory drug, sympathomimetic drug, cholinomimetic drug, adrenergic agonist, adrenergic antagonist, analgesic/antipyretic, anesthetic, antiasthamatic, antibiotic, antidepressant, antidiabetic, antifungal agent, antihypertensive agent, anti-inflammatory, antineoplastic, antianxiety agent, antipsychotics, immunosuppressant agent, antimigraine agent, sedatives/hypnotic, antianginal agent, antipsychotic agent, antimanic agent, antiarrhythmic, antiarthritic agent, antigout agent, anticoagulant, thrombolytic agent, antifibrinolytic agent, hemorheologic agent, antiplatelet agent, anticonvulsant, antiparkinson agent, antihistamine/antipruritic, agent useful for calcium regulation, antibacterial agent, antiviral agent, antimicrobial, anti-infective, bronchodialator, hormone, hypoglycemic agent, hypolipidemic agent, protein, nucleic acid, agent useful for erythropoiesis stimulation, antiulcer/antireflux agent, antinauseant/antiemetic, oil-soluble vitamin, or their pharmaceutically acceptable salts, esters, amides, polymorphs, solvates, hydrates, analogues, enantiomers, tautomeric forms or mixtures thereof, used either alone or in combination thereof. Preferably the other active agent useful in the present invention alongwith mycophenolate sodium is an immunosuppressant such as cyclosporine or a corticosteroid.

It might however be understood that the selection of in-vitro dissolution study media, the parameters and apparatus is made in such a manner so as to provide a scientific rationale to the intended study and/or a logical correlation to the in-vivo data as understood by one skilled in art, and any modifications in such study either in-vitro or in-vivo is within the purview of present invention. Hence the dissolution test of the compositions according to the present invention might be conducted in various apparatus such as USP Apparatus-I, II or III, or any other apparatus or modifications of known dissolution testing apparatus.

The composition of the present invention is prepared by using formulation techniques aimed at releasing of the immunosuppressant active agent in a manner such that the bioavailability of dosage form thus obtained is at least comparable to a conventional immediate release dosage form. Particularly the release of mycophenolate sodium from the dosage form of the present invention is controlled in a such a manner by using one or more release controlling materials alongwith one or more pharmaceutically acceptable excipient(s) so that therapeutically effective plasma concentration of the active agent can be obtained without any undesirable side effects for an extended period of time thus leading to improved patient compliance.

In an embodiment, the dosage form composition comprises mycophenolate sodium as the active agent in at least 0.1% by weight of the composition. In another embodiment, the pharmaceutical composition according to the present invention comprises mycophenolate sodium as the active agent in an amount of about 1% by weight to about 99% by weight of the composition alongwith one or more release controlling material(s) in an amount of about 1% by weight to about 70% by weight of the composition and one or pharmaceutically acceptable excipient(s) in an amount of about 1% by weight to about 99% by weight of composition.

In an embodiment, the present invention provides novel pharmaceutical composition comprising mycophenolate sodium as the active agent; at least one pH independent polymer(s) and at least one lipid agent(s) as release controlling materials, optionally with other pharmaceutically acceptable excipient(s), wherein the said composition provides a release of not more than about 50% w/w of the active agent within 2 hours, when subjected to an in-vitro dissolution test using USP Apparatus-I (Basket method, 100 rpm) and using 0.1 N HCl as dissolution medium maintained at about 37±0.5° C.

In another embodiment, the present invention provides novel pharmaceutical composition comprising mycophenolate sodium as the active agent; at least one pH independent polymer(s) and at least one gum(s) as release controlling materials, optionally with other pharmaceutically acceptable excipient(s), wherein the said composition provides a release of not more than about 50% w/w of the active agent within 2 hours, when subjected to an in-vitro dissolution test using USP Apparatus-I (Basket method, 100 rpm) and using 0.1 N HCl as dissolution medium maintained at about 37±0.5° C.

Oral delivery of the pharmaceutical compositions of the present invention can include extended release formulations, including extended release formulations well known in the art, providing prolonged or sustained delivery of the drug to the gastrointestinal tract by any number of mechanisms. Such prolonged or sustained release mechanisms can include, but are not limited to, pH sensitive release from the dosage form based on the changing pH of the gastrointestinal tract; slow erosion of a tablet or capsule; retention in the stomach based on the physical properties of the formulation; bioadhesion of the dosage form to the mucosal lining of the intestinal tract; or enzymatic release of the active agent mycophenolate sodium from the dosage form. The intended effect is to extend the time period over which the active agent is delivered to site of action by manipulation of dosage form compositions.

One type of extended release composition, for example, achieves extended release by use of a matrix tablet composition. Suitable matrix forming materials are waxes (e.g., carnauba, bees wax, paraffin wax, ceresine, shellac wax, fatty acids, and fatty alcohols); oils, hardened oils or fats (e.g., hardened rapeseed oil, castor oil, beef tallow, palm oil, and soya bean oil); polymers (e.g., hydroxypropyl cellulose, hydroxyethyl cellulose, polyvinylpyrrolidone, hydroxypropyl methyl cellulose, polyethylene glycol, methacrylates (PMMA), polycarbophils and carbomers); alginates; xanthum gums; and other carrier materials known to those of ordinary skill in the art. Other suitable matrix tableting materials include, but are not limited to, microcrystalline cellulose, powdered cellulose, hydroxypropyl cellulose, and ethyl cellulose. Other types of extended release compositions may achieve controlled release by use of granulates, coated powders, pellets, or the like, by use of multi-layering, and/or by used of suitable coatings. Still other extended release compositions include an osmotic pump, or combinations of the above. Extended release compositions can be made by one or more techniques such as prilling, spray drying, pan coating, melt granulation, granulation, wurster coating, tangential coating, top spraying, tableting, extruding, coacervation and the like. The particle size of the extended release components other than active agent in the dosage form depends on the technology used. The particle sizes can range from submicron to 1000 micron for powder technologies (mixtures, spray drying, dispersions, and the like); 5-1900 microns for coating technologies (wurster, top spray, bottom spray, spray drying, extrusion, layering, and the like); and 0.1 mm to 50 mm for tableting technologies. The compositions can include the active agent in a micronized form. Where the composition is in the form of a pellet product, the pellets can be presented in a sachet, capsule or tablet.

In a further embodiment, a plurality of elements containing active agent, or cores, are prepared by extrusion/spheronization, or by layering the active agent (or a blend of active agent with other carrier materials) onto inert carriers by various processes. The cores can contain the active agent at the required potency according to the particular active agent dose, required size, required presentation, and subsequent processes (coating and the like). The cores can contain active agent in the range of about 0.1% to about 100%, depending on the required dose, potency, manufacturing method, and other properties. The controlled release form can be in the form of coated beads or granules of the active agent. The controlled release portion of the dose can be provided by a controlled release core as described above, or a controlled release core that is further modified by overcoating. Preferably, the extended release compositions provide a therapeutic effect over a period greater than about 12 hours, with a sustained therapeutic effect for a period of 12 to 24 hours being especially preferred.

In an embodiment wherein the composition of the present invention is in the form of a tablet, such tablet when exposed to aqueous media, such as in the gastrointestinal tract, the tablet surface wets and the release controlling material(s) begins to partially hydrate forming an outer gel layer. This outer gel layer becomes fully hydrated and begins to erode into the aqueous fluids. Water continues to permeate toward the core of the tablet permitting another gel layer to form beneath the dissolving outer gel layer. These successive concentric gel layers sustain uniform release of the active agent by diffusion from the gel layer and exposure through tablet erosion. Changes in the tablet size and shape can affect the surface to volume ratio of the tablet and therefore the active agent release kinetics from the hydrophilic matrix of the tablet. The release controlling material(s) useful in the present invention preferably comprises a polymeric material selected from but not limited to the group comprising pH dependent polymers such as alginates, carbomers, cellulose propionate (lower, medium or higher molecular weight), cellulose acetate propionate, cellulose acetate butyrate, cellulose triacetate or methacrylic acid polymers or a mixture thereof used either alone or in combination thereof; pH independent polymers such as acrylate or methacrylate polymers, or cellulosic polymers; soluble or insoluble polymers; swellable polymers; hydrophilic polymers; hydrophobic polymers; ionic polymers such as calcium carboxymethylcellulose or sodium carboxymethylcellulose; non-ionic polymers such as hydroxypropyl methylcellulose (HPMC K100CR); synthetic or natural polysaccharide selected from the group comprising alkylcelluloses, hydroxyalkyl celluloses, cellulose ethers, cellulose esters, nitrocelluloses, dextrin, agar, carrageenan, pectin, furcellaran, starch and starch derivatives, and mixtures thereof; cellulosic polymer, methacrylate polymer, carboxyvinyl polymer (Carbopol 71G), Copolymers of acrylate and methacrylates with quarternary ammonium group (Eudragit®), polyvinylpyrrolidone (PVP), polyvinylpyrrolidone-polyvinylacetate polymer (PVP-PVA) copolymer, ethylcellulose, cellulose acetate, poly(alkyl methacrylate), poly(isodecyl methacrylate), poly (lauryl methacrylate), poly(phenyl methacrylate), poly(alkyl acrylate), poly(octadecyl acrylate), poly(ethylene), poly (alkylene), poly(alkylene oxide), poly(alkylene terephthalate), poly(vinyl isobutyl ether), poly(vinyl acetate), poly (vinyl chroride) and polyurethane or a mixture thereof used either alone or in combination thereof. In a further embodiment, the release controlling material(s) useful in the present invention is a gum selected from but not limited to a group comprising xanthan gum, guar gum, gum arabic, carrageenan gum, karaya gum, locust bean gum, acacia gum, tragacanth gum, agar and the like or mixtures thereof. In an embodiment, the release controlling material(s) useful in the present invention is a lipid agent selected from but not limited to a group comprising glyceryl behenate such as Compritol® ATO888, Compritol® HD ATO 5, and the like; hydrogenated vegetable oil such as hydrogenated castor oil e.g. Lubritab®; glyceryl palmitostearate such as Precirol® ATO 5 and the like, or mixtures thereof.

The pharmaceutically acceptable excipient(s) useful in the composition of the present invention are selected from but not limited to a group of excipients generally known to persons skilled in the art e.g. diluents such as lactose (Pharmatose DCL21), starch, mannitol, sorbitol, dextrose, microcrystalline cellulose, dibasic calcium phosphate, sucrose-based diluents, confectioner's sugar, monobasic calcium sulfate monohydrate, calcium sulfate dihydrate, calcium lactate trihydrate, dextrates, inositol, hydrolyzed cereal solids, amylose, powdered cellulose, calcium carbonate, glycine, and bentonite; disintegrants; binders; fillers; bulking agent; organic acid(s); colorants; stabilizers; preservatives; lubricants; glidants/antiadherants; chelating agents; vehicles; bulking agents; stabilizers; preservatives; hydrophilic polymers; solubility enhancing agents such as glycerin, various grades of polyethylene oxides, transcutol and glycofurol; tonicity adjusting agents; local anesthetics; pH adjusting agents; antioxidants; osmotic agents; chelating agents; viscosifying agents; wetting agents; emulsifying agents; acids; sugar alcohol; reducing sugars; non-reducing sugars and the like used either alone or in combination thereof. The disintegrants used in the present invention include but not limited to starch or its derivatives, partially pregelatinized maize starch (Starch 1500®), croscarmellose sodium, sodium starch glycollate, clays, celluloses, alginates, pregelatinized corn starch, crospovidone, gums and the like used either alone or in combination thereof. The lubricants used in the present invention include but not limited to talc, magnesium stearate, calcium stearate, sodium stearate, stearic acid, hydrogenated vegetable oil, glyceryl behenate, glyceryl behapate, waxes, Stearowet, boric acid, sodium benzoate, sodium acetate, sodium chloride, DL-leucine, polyethylene glycols, sodium oleate, sodium lauryl sulfate, magnesium lauryl sulfate and the like used either alone or in combination thereof. The anti-adherents or glidants useful in the present invention are selected from but not limited to a group comprising talc, corn starch, DL-leucine, sodium lauryl sulfate, and magnesium, calcium and sodium stearates, and the like or mixtures thereof. The vehicles suitable for use in the present invention can be selected from but not limited to a group comprising dimethylacetamide, dimethylformamide and dimethylsulphoxide, N-methyl pyrrolidone, benzyl benzoate, benzyl alcohol, ethyl oleate, polyoxyethylene glycolated castor oils (commercially available as Cremophor® EL), polyethylene glycol MW 200 to 6000, propylene glycol, hexylene glycols, butylene glycols and glycol derivatives such as polyethylene glycol 660 hydroxystearate (commercially available as Solutrol® HS15). In another embodiment of the present invention, the compositions may additionally comprise an antimicrobial preservative such as Benzyl alcohol preferably at a concentration of 2.0% v/v of the composition. In an embodiment of the present invention, the composition may additionally comprise a conventionally known antioxidant such as ascorbyl palmitate, butylhydroxyanisole, butylhydroxytoluene, propyl gallate and α-tocopherol. In another embodiment, the dosage form of the present invention additionally comprises at least one wetting agent(s) such as a surfactant selected from a group comprising anionic surfactants, cationic surfactants, non-ionic surfactants, zwitterionic surfactants or mixtures thereof. The wetting agents are selected from but not limited to a group comprising oleic acid, glyceryl monostearate, sorbitan monooleate, sorbitan monolaurate, triethanolamine oleate, polyoxyethylene sorbitan monooleate, polyoxyethylene sorbitan monolaurate, sodium oleate, sodium lauryl sulfate and the like or mixtures thereof. In yet another embodiment, the dosage form of the present invention additionally comprises at least one complexing agent such as cyclodextrin selected from a group comprising but not limited to alpha-cyclodextrin, beta-cyclodextrin, betahydroxy-cyclodextrin, gamma-cyclodextrin, and hydroxypropyl beta-cyclodextrin, or the like. In yet another embodiment, the dosage form of the present invention additionally comprises of lipids include but not limited to glyceryl behenate such as Compritol® ATO888, Compritol® HD ATO 5, and the like; hydrogenated vegetable oil such as hydrogenated castor oil e.g. Lubritab®; glyceryl palmitostearate such as Precirol® ATO 5 and the like, or mixtures thereof.

The amount of mycophenolate sodium to be incorporated into the pharmaceutical composition of the present invention can vary over a wide range depending on known factors such as, for example, the intended use i.e. prophylactic or therapeutic, disease/disorder to be treated, the severity of the disease/disorder, the patient's body weight, the dosage form, the chosen route of administration and the number of administration per day. However, selection of optimum amount is simple and routine for a person skilled in the art. Typically the amount of mycophenolate sodium would be equivalent to about 10 mg to about 1000 mg of mycophenolic acid. The pharmaceutical composition preferably provides a daily dosage of mycophenolate sodium in an amount equivalent to about 10 mg to about 1000 mg of mycophenolic acid. A daily dose of about 0.14 to about 50.00 mg/kg body weight may be appropriate. The daily dose can be administered in one to two doses per day, preferably one dose per day.

In an embodiment, the compositions of the present invention comprising mycophenolate sodium as active agent, releases the active agent throughout the gastro-intestinal tract (GIT). Preferably the compositions are designed in such a manner so as to release a sufficient amount of the active agent in the lower part of the GIT and a substantial amount of the active agent in the upper part of the intestine, e.g. in the duodenum, jejunum and/or ileum. The release of mycophenolate sodium from the dosage form compositions of the present invention are designed in such a manner so that the said active is absorbed continuously throughout the GIT thus producing desired concentrations of the active in the blood and at the same time devoid of any substantial gastro-intestinal side effects associated with the active agent. Further, the compositions release the active agent in a manner such that it is effective, safe and well-tolerated particularly for immunosuppressive indications especially for the treatment or prevention of organ, tissue or cellular allograft or xenograft rejection, e.g. after transplant, or the treatment or prevention of immune-mediated diseases. In another embodiment, the compositions of the present invention may be formulated to disintegrate or erode relatively slowly in the lower part of the GIT such as the stomach as compared to its disintegration or erosion in the upper part of the GIT.

In an embodiment, the present invention provides a pharmaceutical composition comprising particulate mycophenolate sodium having a $D_{90}$ particle size of about 0.1 to about 300 microns, in an amount equivalent to about 10 mg to about 1000 mg of mycophenolic acid, at least one release controlling material(s), optionally alongwith one or more pharmaceutically acceptable excipient(s), wherein not more than about 50% w/w of the active agent is released within 2 hours, when the composition is subjected to an in-vitro dissolution test using USP Apparatus-I (Basket method, 100 rpm) and using 0.1 N HCl as dissolution medium maintained at about 37±0.5° C.

In an embodiment, the pharmaceutical composition according to the present invention comprises about 1% by weight to about 95% by weight of mycophenolate sodium; about 0.001% by weight to about 75% by weight of diluent(s); about 1% by weight to about 75% by weight of release controlling material(s); about 0% by weight to about 20% by weight of binder(s); and optionally about 0.1% by weight to about 70% by weight of at least one lipophilic material(s) and optionally 0.01% by weight to about 15% by weight of a lubricant. In an embodiment, when the composition of the present invention is formulated as a tablet dosage form, the lipophilic material(s) is present intragranularly or extragranularly or both intra and extragranularly but more preferably extragranularly alongwith the lubricant(s).

In a further embodiment, the pharmaceutical composition according to the present invention comprises mycophenolate sodium in an amount equivalent to about 10 mg by weight to about 1000 mg by weight of mycophenolic acid; about 0 mg by weight to about 2000 mg by weight of diluent(s); about 1 mg by weight to about 1500 mg by weight of release controlling polymer(s); about 0 mg by weight to about 500 mg by weight of binder(s); and optionally about 1 mg by weight to about 1500 mg by weight of at least one lipophilic material(s) and optionally about 1 mg by weight to about 500 mg by weight of a lubricant. In a further embodiment, the release controlling material is an acrylate or a methacrylate polymer or copolymer or a mixture of such polymers. In a still further embodiment, the binder is an acrylate or a methacrylate polymer or copolymer or a mixture of such polymers.

In still further embodiment, the pharmaceutical composition comprises one or more of a lipophilic material selected from but not limited to a group comprising glyceryl behenate, an acrylate or a methacrylate polymer or copolymer such as Eudragit®, a cellulosic polymer such as hydroxymethylpropylcellulose, a gum such as xanthan gum, or mixtures thereof. In another embodiment, one or more of a lipohpilic material such as glyceryl behenate, an acrylate or a methacrylate polymer or copolymer such as Eudragit®, a cellulosic polymer such as hydroxymethylpropylcellulose, a gum such as xanthan gum, or mixtures thereof is present as a lubricant composition which is added extragranularly to make the composition. In a further embodiment, the pharmaceutical composition is a coated or uncoated solid unit dosage form such as tablet.

In another embodiment, the extended release compositions of the present invention comprises a core and at least one coating such that the active agent mycophenolate sodium is either present in the core or the coat or in both. The coating also contributes in extending the release of the active agent from the compositions. The coating is applied on the core compositions from a solution and/or suspension preferably in an aqueous or an organic solvent. Examples of film-forming agents which are suitable for use in the coating composition in accordance with the present invention are agents selected from the group comprising of cellulose derivatives such as, e.g., ethylcellulose, cellulose acetate, cellulose propionate, cellulose butyrate, cellulose valerate, cellulose acetate propionate; methacrylic polymers; acrylic polymers such as, e.g., polymethyl methacrylate; vinyl polymers such as, e.g., polyvinyl acetate, polyvinyl formal, polyvinyl butyryl, vinyl chloride-vinyl acetate copolymer, vinyl acetate polymers and copolymers such as Kollicoat®SR 30D which is polyvinyl acetate (~27% w/w) stabilized with polyvinylpyrrolidone (~2-5% w/w) and sodium lauryl sulfate (~0.3% w/w), copolymer of polyvinyl alcohol-polyethylene glycol (Kollicoat®IR), ethylene-vinyl acetate copolymer, vinyl chloride-propylene-vinyl acetate copolymer; silicon polymers such as, e.g., ladder polymer of sesquiphenyl siloxane, and colloidal silica; polycarbonate; polystyrene; polyester; coumarone-indene polymer; polybutadiene; and other high molecular synthetic polymers, or mixtures thereof.

In an embodiment, the acrylic polymer is comprised of one or more ammonio methacrylate copolymers. In one preferred embodiment, the acrylic coating is an acrylic resin lacquer used in the form of an aqueous dispersion, such as that which is commercially available from Rohm Pharma under the tradename Eudragit®. In further preferred embodiments, the acrylic coating comprises a mixture of two acrylic resin lacquers such as Eudragit® RL 30D and Eudragit® RS 30D, which are copolymers of acrylic and methacrylic esters with a low content of quaternary ammonium groups. Eudragit® RL/RS mixtures are insoluble in water and in digestive fluids. However, coatings formed from the same are swellable and permeable in aqueous solutions and digestive fluids. Other polymers such as Eudragit® RL e.g. Eudragit® RLPO, and Eudragit® RS e.g. Eudragit® RSPO or their suitable mixtures can be used to obtain the extended release composition of the present invention having a desirable dissolution profile. Alternatively a mixture of Eudragit® polymer and a cellulosic polymer such as hydroxypropyl methylcellulose can be used as the coating material. Still further, an extended release composition may also be prepared by using a retardant coating based on Eudragit® NE 30D, which is a neutral resin. Other coating materials such as ethylcellulose or water-soluble coating materials such as water-soluble cellulose derivatives, e.g. hydroxypropylcellulose, carboxymethylcellulose, methylcellulose, propylcellulose, hydroxyethylcellulose, carboxyethylcellulose, carboxymethyl hydroxyethylcellulose, hydroxymethylcellulose, carboxymethyl ethylcellulose, methylhydroxy propylcellulose or hydroxypropyl methylcellulose may be employed in the present invention.

The amount of coating applied is adapted so as to obtain a predetermined dissolution characteristic of the novel extended release composition. The percentage by weight of the coating on the individual unit dosage form is about 0.01-30% w/w of the composition. The amount of coating applied depends on the predetermined dissolution characteristics of the particular core composition and the desired release profile. However, the amount of coating applied is such that there will be no rupturing problems. The coating may be admixed with various excipients such as plasticizers, anti-adhesives such as, e.g., colloidal silicon dioxide, inert fillers, and pigments or mixtures thereof in a manner known per se. Tackiness of the water-dispersible film-forming substances may be overcome by simply incorporating an anti-adhesive in the coating. The anti-adhesive is preferably a finely divided, substantially insoluble, pharmaceutically acceptable non-wetting powder having anti-adhesive properties in the coating. Examples of anti-adhesives are metallic stearates such as magnesium stearate or calcium stearate, microcrystalline cellulose, or mineral substances such as calcite, substantially water-insoluble calcium phosphates or substantially water-insoluble calcium sulphates, colloidal silica, titanium dioxide, barium sulphates, hydrogenated aluminium silicates, hydrous aluminium potassium silicates and talc.

Examples of plasticizers for use in accordance with the present invention include triacetin, acetylated monoglyceride, rape oil, olive oil, sesame oil, acetyl tributyl citrate, acetyl triethyl citrate, glycerin, sorbitol, diethyl oxalate, diethylmalate, diethylmaleate, diethylfumarate, diethylsuccinate, diethylmalonate, dioctylphthalate, dibutylsebacetate, triethylcitrate, tributylcitrate, glyceroltributyrate, polyethyleneglycol, propyleneglycol, 1,2-propyleneglycol, dibutyl sebacate, diethyl sebacate and mixtures thereof. The plasticizer is normally incorporated in an amount of less than about 20% by weight, calculated on the dry matter content of the coating composition.

In an embodiment the coating provided on the core compositions according to the present invention is not an enteric coating.

The extended release formulation according to the present invention refers to a formulation wherein the active agent is released and provided for absorption over a longer period of time than from a conventional dosage form, i.e. to a formulation which provides a modified release profile of the active agent contained therein. Further, in an embodiment, the novel extended release compositions of the present invention comprising mycophenolate sodium as active agent are designed to contain substantially higher concentrations of the active agent in a single unit dosage form and are prepared in such a manner as to affect sustained or slow release of the active agent into the GIT of a subject over an extended period of time. Such compositions comprising a substantially high dose of mycophenolate sodium that are safe, tolerable, effective and easy-to-manufacture had not been achieved earlier which was one of the major limitation of the prior art; however the inventors of the present invention have been able to formulate the novel compositions comprising a substantially high dose of mycophenolate sodium based on extensive research and experimentation. In an embodiment of the present invention, the drug levels are maintained above the lower level of the prophylactic/therapeutic plasma concentration for longer periods of time by giving larger doses of the novel compositions according to the present invention. In an embodiment, the extended release compositions of the present invention may be designed to rapidly release a fraction of a total drug dose (loading dose) which will provide a desired pharmacological response as fast as possible.

The oral extended release compositions of the present invention are well-absorbed and possess other inherent advantages over conventional, immediate release dosage forms. A less frequent dosing of a medicament, as is required by a sustained release dosage form, increases the resultant patient compliance, provides a more sustained drug blood level response, and effects therapeutic action with less ingestion of a drug, thereby mitigating many potential side effects. By providing a slow and steady release of mycophenolate sodium over time, absorbed drug concentration spikes are mitigated or eliminated by affecting a smoother and more sustained blood level response.

However, whichever method of extended release is utilized in the pharmaceutical formulation of the present invention, such as the diffusion of the active agent through the coating, erosion of the coating through which the active agent passes, diffusion of the active agent from a monolithic device, to name a few, the extended release composition results in a uniform and constant dissolution of mycophenolate sodium from the pharmaceutical formulation and is thus effective for an extended period of time. Further, the extended release compositions of the present invention are easy to formulate and the process of preparation is reproducible.

After oral administration, the extended release compositions comprising mycophenolate sodium as active agent in accordance with the invention characteristically releases the active agent in a sustained manner and the pharmaceutical activity maintains for a long period. In accordance with this invention, the frequency of administration of mycophenolate sodium can be decreased. More particularly, it has become possible to provide a pharmaceutical formulation containing mycophenolate sodium which may be administered only once a day. Furthermore, it is by now possible to provide a pharmaceutical composition which is free from the risk for undesired effects caused by a transiently excessive concentration and insures an expression of pharmacological efficacy over a sufficiently extended time period.

In another embodiment is provided a process of preparation of the composition of the present invention which comprises treating the active agent mycophenolate sodium alongwith at least one release controlling material(s) which is hydrophilic or hydrophobic or mixtures thereof, optionally adding one other active agent(s), optionally alongwith one or more pharmaceutically acceptable excipient(s), and formulating into a suitable dosage form.

In an embodiment, the pharmaceutical composition of the present invention is preferably formulated as an oral dosage form such as tablets, capsules, patches and the like. In an embodiment, the composition of the present invention is in the form of tablets. The tablets can be prepared by either direct compression, dry compression (slugging), or by granulation. The granulation technique is either aqueous or non-aqueous. The non-aqueous solvent used is selected from a group comprising ethanol, isopropyl alcohol, and acetone or methylene chloride. In an embodiment, the compositions of the present invention are in the form of compressed tablets, molded tablets, layered tablets, matrix tablets, or products prepared by extrusion or film cast technique, and the like, preferably made into a homogeneous matrix system in the form of single unit dosage form such as a tablet or capsule. "Homogeneous matrix system" as described herein in the specification means the active; the polymer(s) and the pharmaceutically acceptable excipients are uniformly dispersed or distributed throughout the dosage form. In an embodiment, the composition of the present invention may be in the particulate form such a powder, granules, beads, pellets, mini-tablets or the like. The compositions may be coated with a 'functional coating'. By the term 'functional coating' it is herein implied that the coating composition does not comprise of a enteric polymer but comprises a part of the active agent(s) and/or the composition comprises excipient(s) which aid in controlling the rate of release of the active agent(s) independent of the pH through GIT pHs and/or the composition comprises additionally another active agent which is different from the active agent present in the core composition. The composition may be formulated as layered tablets comprising at least two layers wherein the same active agent is present in all the layers exhibiting different release profiles or one or more additional active agent(s) is present in the layers exhibiting different release profiles. The coating composition employed may be an aqueous, non-aqueous or a hydro-alcoholic system. The solvents used to prepare a non-aqueous coating composition is selected from but not limited to a group comprising dehydrated alcohol, isopropyl alcohol, methylene chloride, acetone or any other solvent known to the art for such use, or mixtures thereof. The coating composition can include an antitack agent such as talc, kaolin, titanium dioxide, silicon dioxide, alumina, starch, polacrilin potassium, microcrystalline cellulose or the like.

In an essential embodiment, the mechanical strength of the composition according to the present invention is sufficiently high to withstand normal handling of a pharmaceutical composition and to enable the composition to be coated using traditional coating equipments well known to a person skilled in the art.

In yet another embodiment, the present invention provides use of the pharmaceutical composition according to the present invention in reducing the variability in absorption of mycophenolate sodium throughout the gastro-intestinal tract by providing a substantially uniform sustained release in-vivo and also reducing the chances of causing any associated gastrointestinal side effects without compromising the bioavailability of said active agent.

In another embodiment of the present invention is provided a method of using the composition of the present invention for the management such as prophylaxis, amelioration and/or treatment of immunosuppressant indicated disease(s)/disorder(s) especially for the treatment or prevention of organ, tissue or cellular allograft or xenograft rejection, e.g. after transplant, or the management of immune-mediated diseases (autoimmune diseases), which comprises administering to a subject in need thereof the composition comprising a pharmaceutically effective amount of mycophenolate sodium as the active agent. In an embodiment, the compositions of the present invention can be used as a medicament. In yet another embodiment of the present invention is provided use of the pharmaceutical composition comprising pharmaceutically effective amount of mycophenolate sodium as the active agent for the preparation of a medicament for the management such as prophylaxis, amelioration and/or treatment of immunosuppressant indicated disease(s)/disorder(s) especially for organ, tissue or cellular allograft or xenograft rejection, e.g. after transplant, or the management of immune-mediated diseases (autoimmune diseases).

In an embodiment, the compositions of the present invention are useful in the treatment and prevention of native or transgenic organ, tissue or cellular allograft or xenograft transplant rejection, e.g. for the treatment of recipients of e.g. heart, lung, combined heart-lung, liver, kidney, skin, pancreatic islet cell, neural cell or corneal transplant; including treatment and prevention of acute rejection; treatment and prevention of hyperacute rejection, e.g. as associated with xenograft rejection; and treatment and prevention of chronic rejection, e.g. as associated with graft-vessel disease. The compositions of the invention are also indicated for the treatment and prevention of graft-versus-host disease, such as following bone marrow transplantation.

In a further embodiment, the compositions of the present invention are also useful in the treatment and prevention of autoimmune diseases, e.g. immune-mediated diseases and inflammatory conditions, in particular inflammatory conditions with an etiology including an immunological component such as arthritis (for example rheumatoid arthritis, arthritis chronica progrediente and arthritis deformans) and rheumatic diseases. Specific immune-mediated diseases for which the compositions of the invention may be employed include, autoimmune hematological disorders, including, but not limited to hemolytic anaemia, aplastic anaemia, pure red cell anaemia and idiopathic thrombocytopenia), systemic lupus erythematosus, polychondritis, sclerodoma, Wegener granulosis, dermatomyositis, polymyositis, chronic active hepatitis, primary bilary cirrhosis, myasthenia gravis, psoriasis, Steven-Johnson syndrome, pemphigus, idiopathic sprue, inflammatory bowel diseases (including e.g. ulcerative colitis and Crohn's disease), endocrine ophthalrriophathy, Graves disease, sarcoidosis, multiple sclerosis, primary biliary cirrhosis, juvenile diabetes (diabetes mellitus type I), non-infectious uveitis (anterior and posterior), keratoconjunctivitis sicca and vernal keratoconjunctivitis, interstitial lung fibrosis, psoriatic arthritis, vasculitides, glomerulonephritides (with and without nephrotic syndrome, e.g. including idiopathic nephrotic syndrome or minimal change nephropathy) and juvenile dermatomyositis.

In a preferred embodiment, the pharmaceutical compositions of the present invention are intended for once-a-day or twice-a-day administration, preferably for once-a-day administration. The once-a-day composition releases the active agent mycophenolate sodium in a desired manner so as to maintain prophylactic and/or therapeutic levels of the active agent in the plasma for extended period of time devoid of any substantial drug related toxicity, and also can be prepared in an easy and cost-effective manner.

The present invention provides once-a-day compositions comprising mycophenolate sodium such that the inter- and intra-patient variability is reduced. Particularly the extended release mycophenolate sodium compositions of the present invention are stable and easily swallowable upon oral administration, possess appreciable bioavailability characteristics, and are well-tolerated and safe. In a preferred embodiment, the oral compositions comprising mycophenolate sodium for prophylactic and/or therapeutic use, can release the drug in a desired manner such as to maintain prophylactic/therapeutic levels of the drug in the plasma for extended period of time but without causing drug related toxicity; and which can be prepared in an easy and cost-effective manner.

In an embodiment of the present invention, the compositions as mentioned hereinafter in Example-1 and Example-2 were subjected to bioavailability study conducted in healthy adult human subjects. The protocol of the study is as follows:

"A randomized, open label, three treatment, three period, three sequence, single dose, crossover comparative bioavailability study was conducted under fasting conditions comparing rate and extent of absorption of two test formulations of Mycophenolate Sodium ER tablets (720 mg) of Panacea Biotec Ltd. with Cellcept® Tablets (2*500 mg) in nine (+3 Standby) healthy adult human subjects. The wash out period was for one week".

Figure 1:
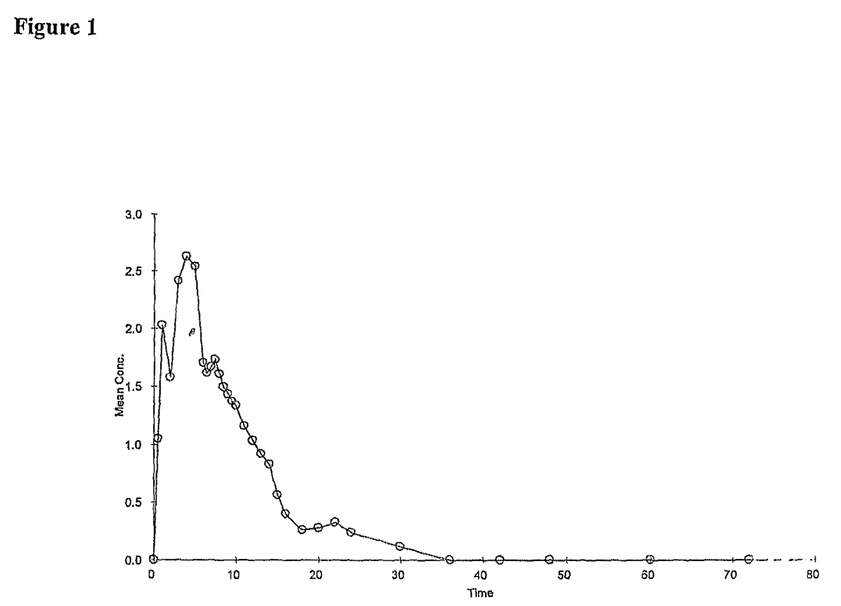
FIG. 1: The said figure shows the plasma concentration vs. time of the composition as mentioned hereinafter in Example-1.
Figure 2:
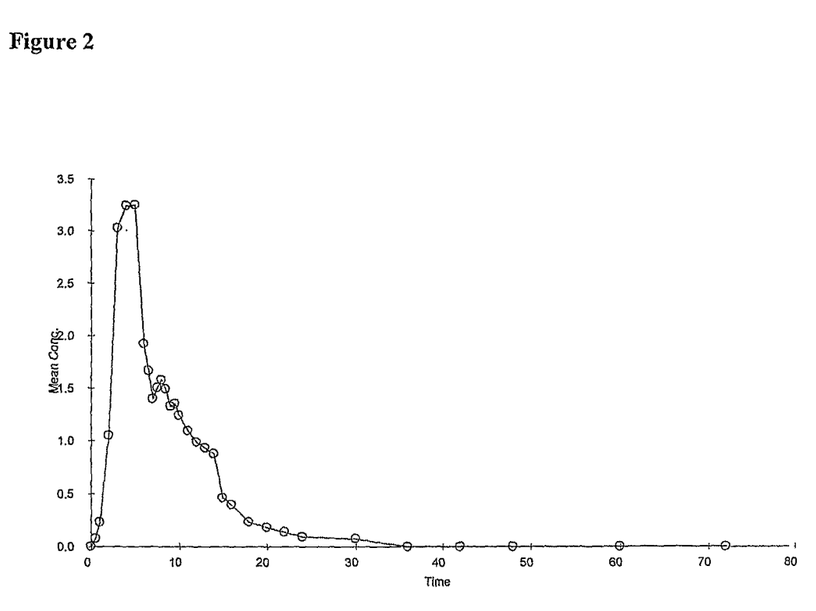
FIG. 2: The said figure shows the plasma concentration vs. time of the composition as mentioned hereinafter in Example-2.

The in-vivo study for compositions as mentioned hereinbefore in Example-1 and Example-2 of the present invention were plotted as plasma concentration vs. time, the result of which is as follows:

| S. No. | Time (hrs.) | Mean Conc. (μg/ml) (Example-1) |
|---|---|---|
| 1. | 0 | 0 |
| 2. | 0.5 | 1.0485 |
| 3. | 1 | 2.0275 |
| 4. | 2 | 1.5765 |
| 5. | 3 | 2.4153 |
| 6. | 4 | 2.628 |
| 7. | 5 | 2.542 |
| 8. | 6 | 1.7023 |
| 9. | 6.5 | 1.6164 |
| 10. | 7 | 1.6693 |
| 11. | 7.5 | 1.7294 |
| 12. | 8 | 1.6087 |
| 13. | 8.5 | 1.496 |
| 14. | 9 | 1.4349 |
| 15. | 9.5 | 1.3708 |
| 16. | 10 | 1.339 |
| 17. | 11 | 1.1609 |
| 18. | 12 | 1.0363 |
| 19. | 13 | 1.9209 |
| 20. | 14 | 0.8293 |
| 21. | 15 | 0.5621 |

-continued

| S. No. | Time (hrs.) | Mean Conc. (µg/ml) (Example-1) |
|---|---|---|
| 22. | 16 | 0.3976 |
| 23. | 18 | 0.2603 |
| 24. | 20 | 0.2788 |
| 25. | 22 | 0.3248 |
| 26. | 24 | 0.2391 |
| 27. | 30 | 0.1143 |
| 28. | 36 | 0 |
| 29. | 42 | 0 |
| 30. | 48 | 0 |
| 31. | 60 | 0 |
| 32. | 72 | 0 |

| S. No. | Time (hrs.) | Mean Conc. (µg/ml) (Example-2 |
|---|---|---|
| 1. | 0 | 0 |
| 2. | 0.5 | 0.0751 |
| 3. | 1 | 0.2274 |
| 4. | 2 | 1.0473 |
| 5. | 3 | 3.0239 |
| 6. | 4 | 3.2384 |
| 7. | 5 | 3.2453 |
| 8. | 6 | 1.9203 |
| 9. | 6.5 | 1.6662 |
| 10. | 7 | 1.3965 |
| 11. | 7.5 | 1.4989 |
| 12. | 8 | 1.5751 |
| 13. | 8.5 | 1.4872 |
| 14. | 9 | 1.3254 |
| 15. | 9.5 | 1.3493 |
| 16. | 10 | 1.2381 |
| 17. | 11 | 1.0897 |
| 18. | 12 | 0.9843 |
| 19. | 13 | 0.9281 |
| 20. | 14 | 0.8722 |
| 21. | 15 | 0.459 |
| 22. | 16 | 0.3949 |
| 23. | 18 | 0.2305 |
| 24. | 20 | 0.1799 |
| 25. | 22 | 0.1361 |
| 26. | 24 | 0.0928 |
| 27. | 30 | 0.0721 |
| 28. | 36 | 0 |
| 29. | 42 | 0 |
| 30. | 48 | 0 |
| 31. | 60 | 0 |
| 32. | 72 | 0 |

It is evident from the plasma concentration profile in healthy adult human subjects as mentioned hereinabove that the absorption of Mycophenolate sodium starts from gastric region (the concentration of MPA at 0.5 h being 1.04 µg/ml and 0.075 µg/ml for Examples 1 and 2 hereinbefore respectively). It can thus be interpreted from the plasma drug concentration time profile that the drug is being absorbed throughout the GIT.

In an embodiment of the present invention, the composition as mentioned hereinafter in Example-1 when tested in vivo exhibits a $C_{max}$ (peak plasma concentration of the drug) of 4.28, $T_{max}$ (time to reach peak plasma concentration) of 3.5 hours, $T_{1/2}$ (plasma elimination half life) of 7.09. Further parameters that were evaluated were $AUC_{0-24}$ (area under the 'plasma concentration versus time' curve from t=0 to time=24) of 25.41, $AUC_{0-\infty}$ (area under the 'plasma concentration versus time' curve from t=0 to time=∞, where '∞' denotes infinity) of 29.17 and $AUC_{last}$ of 25.86.

In another embodiment of the present invention, the composition as mentioned hereinafter in Example-2 when tested in vivo exhibits a $C_{max}$ (peak plasma concentration of the drug) of 4.39, $T_{max}$ (time to reach peak plasma concentration) of 4.56 hours, $T_{1/2}$ (plasma elimination half life) of 6.18. Further parameters that were evaluated were $AUC_{0-24}$ (area under the 'plasma concentration versus time' curve from t=0 to time=24) of 22.8, $AUC_{0-\infty}$ (area under the 'plasma concentration versus time' curve from t=0 to time=∞, where '∞' denotes infinity) of 25.18 and $AUC_{last}$ of 23.1.

The examples given below serve to illustrate embodiments of the present invention. However they do not intend to limit the scope of the present invention.

EXAMPLES

Example-1

| S. No. | Ingredient | Quantity/ tablet (mg) |
|---|---|---|
| | Intragranular addition | |
| 1. | Mycophenolate sodium (equivalent to 720 mg of mycophenolate sodium) | 780.05 |
| | Granulating agent | |
| 2. | Polyvinyl pyrrolidone | 4.9 |
| 3. | Ethanol | q.s. |
| 4. | Water | q.s. |
| | Extragranular addition | |
| 5. | Lactose anhydrous | 24.9 |
| 6. | Ammonio methacrylate copolymer (Eudragit ® RSPO) | 40 |
| 7. | Xanthan gum | 20 |
| 8. | Hydroxypropyl methylcellulose | 120 |
| 9. | Magnesium stearate | 10 |
| | Coating | |
| 10. | Opadry brown | 20 |
| 11. | Purified water | q.s. |

Procedure i) Mycophenolate sodium was weighed and granulated with polyvinyl pyrrolidone in ethanol:water mixture and the wet mass was passed through sieves and dried.

ii) The granules of step (i) were mixed with lactose anhydrous, hydroxypropyl methylcellulose, ammonio methacrylate copolymer and xanthan gum and lubricated with half the quantity of magnesium stearate.

iii) The granules of step (ii) were slugged and the slugs were deslugged to get desired granules.

iv) The remaining quantity of mesh #40 passed magnesium stearate was mixed with the granules of step (iii) and compressed to obtain tablets.

v) The tablets of step (iv) were coated with aqueous dispersion of Opadry brown.

Dissolution Profile:

| S. No. | Time (hr) | % drug released Parameters: USP Apparatus II, 100 rpm, 0.1N HCl followed by pH 6.8 Phosphate Buffer |
|---|---|---|
| 1. | 1 | 0.6 |
| 2. | 2 | 1.0 |
| 3. | 3 | 16.0 |
| 4. | 4 | 27.8 |
| 5. | 6 | 47.3 |
| 6. | 8 | 65.4 |
| 7. | 10 | 80.9 |
| 8. | 12 | 89.7 |
| 9. | 14 | 96.4 |
| 10. | 16 | 97.3 |
| 11. | 20 | 99.6 |

Example-2

| S. No. | Ingredient | Quantity/ tablet (mg) |
|---|---|---|
| | Intragranular addition | |
| 1. | Mycophenolate sodium (equivalent to 720 mg of mycophenolate sodium) | 780.05 |
| 2. | Lactose anhydrous | 5.71 |
| 3. | Glyceryl behenate | 130.54 |
| 4. | Colloidal silicon dioxide | 9.8 |
| 5. | Ammonio methacrylate copolymer (Eudragit ® RSPO) | 39.20 |
| | Granulating agent | |
| 6. | Polyvinyl pyrrolidone | 4.90 |
| 7. | Ethanol:Dimineralised water | 1.38 |
| | Extragranular addition | |
| 8. | Magnesium stearate | 9.80 |
| | Coating composition | |
| 9. | Polyvinyl acetate aqueous dispersion (Kollicoat ® SR 30D) | 37.28 |
| 10. | Polyvinyl alcohol polyethylene glycol copolymer (Kollicoat ® IR) | 5.33 |
| 11. | Polyethylene glycol (PEG 400) | 1.60 |
| 12. | Talc | 4.79 |
| 13. | Water | 5 |

Procedure i) Mycophenolate sodium, lactose anhydrous, ammonio methacrylate copolymer and glyceryl behenate were weighed and sifted through mesh#40 sieve and mixed together.

ii) Powder blend of step (i) was granulated with ethanol: water mixture and dried, passed through suitable sieves to get the granules.

iii) The granules of step (ii) were lubricated with mesh#40 passed magnesium stearate and compressed to obtain tablets.

iv) Polyvinyl alcohol polyethylene glycol copolymer and polyethylene glycol were dissolved in water by continuous stirring.

v) Polyvinyl acetate aqueous dispersion and talc were dispersed in the solution of step (iv) under continuous stirring.

vi) The tablets of step (iii) were finally coated with aqueous dispersion of material of step (v).

Dissolution Profile:

| S. No. | Time (hr) | % drug released Parameters: USP Apparatus II, 100 rpm, 0.1N HCl followed by pH 6.8 Phosphate Buffer |
|---|---|---|
| 1. | 1 | 0.1 |
| 2. | 2 | 0.1 |
| 3. | 3 | 20.2 |
| 4. | 4 | 34.4 |
| 5. | 6 | 54.5 |
| 6. | 8 | 67.6 |
| 7. | 10 | 75.5 |
| 8. | 12 | 80.2 |
| 9. | 14 | 84.0 |
| 10. | 16 | 86.7 |
| 11. | 20 | 88.9 |
| 12. | 24 | 92.7 |
| 13. | 28 | 94.6 |
| 14. | 32 | 97.4 |

Example-3

| S. No. | Ingredient | Quantity/ tablet (mg) |
|---|---|---|
| | Intra-granular addition | |
| 1. | Mycophenolate sodium (equivalent to 720 mg of mycophenolate sodium) | 770.35 |
| 2. | Lactose anhydrous | 13.96 |
| 3. | Colloidal silicon dioxide (Aerosil 200) | 5.25 |
| 4. | Polyvinyl pyrrolidone (PVP K-90) | 26.25 |
| 5. | Hydroxypropyl methylcellulose (HPMC K-100 CR) | 183.75 |
| 6. | Polyethylene oxide (Polyox WSR 301) | 26.25 |
| | Granulating agent | |
| 7. | Polyvinyl pyrrolidone (PVP K-30) | 10.5 |
| 8. | Isopropyl alcohol | 390 (ml) |
| | Extra-granular addition | |
| 9. | Magnesium stearate | 10.5 |

Procedure:

i) Mycophenolate sodium and Lactose anhydrous were passed through suitable sieve and granulated with aqueous Eudragit® NE30D dispersion containing Copovidone and dried. Mycophenolate sodium, lactose anhydrous, colloidal silicon dioxide, polyvinyl pyrrolidone (PVP K-90), polyethylene oxide and hydroxypropyl methylcellulose were weighed and passed through #40 s.s. sieve and mixed for 5 mins.

ii) Polyvinyl pyrrolidone (PVP K-30) was weighed and dissolved in isopropyl alcohol under stirring.

iii) The blend of step (iii) was granulated using the solution of step (ii), dried and passed through suitable sieves to obtain granules.

iv) Step (iii) granules were lubricated with mesh #40 passed magnesium stearate and compressed to obtain tablets.

Dissolution Profile:

| S. No. | Time (hr) | % drug released Parameters: USP Apparatus I, 100 rpm, 0.1N HCl followed by pH 6.8 Phosphate Buffer |
|---|---|---|
| 1. | 1 | 0.14 |
| 2. | 2 | 0.63 |
| 3. | 3 | 8.2 |
| 4. | 4 | 13.3 |
| 5. | 6 | 21.3 |
| 6. | 8 | 36.1 |
| 7. | 10 | 49.4 |
| 8. | 12 | 62.2 |
| 9. | 14 | 72.9 |
| 10. | 16 | 82.2 |
| 11. | 20 | 90.0 |
| 12. | 24 | 96.4 |

Example-4

| S. No. | Ingredient | Quantity/tablet (mg) |
|---|---|---|
| 1. | Mycophenolate sodium (equivalent to 720 mg of mycophenolate sodium) | 773.5 |
| 2. | Lactose anhydrous | 2.8 |
| 3. | Glyceryl behenate (Compritol ® ATO888) | 96.5 |
| 4. | Kollicoat ® SR 30D | 57.9 |
| 5. | 1N HCl solution | q.s. |
| 6. | Magnesium stearate | 19.3 |

Procedure:

i) Mycophenolate sodium, lactose anhydrous and Compritol® ATO888 were weighed, passed through mesh #40 sieve and mixed for 5 mins.

ii) Kollicoat®SR 30D was weighed and the pH was adjusted with 1N HCl solution to pH 2.0.

iii) The blend of step (i) was granulated using the dispersion of step (ii) and dried, passed through mesh #24 sieve to obtain the granules.

iv) Step (iii) granules were lubricated with mesh #40 passed magnesium stearate and compressed with caplet shaped punch to obtain tablets.

Dissolution Profile:

| S. No. | Time (hr) | % drug released Parameters: USP Apparatus I, 100 rpm, 0.1N HCl (0-2 Hrs) followed by pH 6.8 Phosphate Buffer |
|---|---|---|
| 1. | 1 | 0.2 |
| 2. | 2 | 0.5 |
| 3. | 3 | 36.4 |
| 4. | 4 | 56.5 |
| 5. | 6 | 76.6 |
| 6. | 8 | 85.9 |
| 7. | 10 | 88.9 |
| 8. | 12 | 89.5 |

Example-5

| S. No. | Ingredient | Quantity/tablet (mg) |
|---|---|---|
| 1. | Mycophenolate sodium (equivalent to 720 mg of mycophenolate sodium) | 773.5 |
| 2. | Lactose anhydrous | 2.8 |
| 3. | Acrylic and methacrylic ester copolymer (Eudragit ® RS30D) | 57.9 |
| 4. | 1N HCl solution | q.s. |
| 5. | Glyceryl behenate (Compritol ® ATO888) | 96.5 |
| 6. | Magnesium stearate | 19.3 |

Procedure:

i) Mycophenolate sodium, lactose anhydrous and Compritol® ATO888 were weighed, passed through mesh #40 sieve and mixed for 5 mins.

ii) Eudragit® RS30D was weighed and the pH was adjusted with 1N HCl solution to pH 2.0.

iii) The blend of step (i) was granulated using the dispersion of step (ii) and dried, passed through mesh #24 sieve to obtain the granules.

iv) Step (iii) granules were lubricated with mesh #40 passed magnesium stearate and compressed with caplet shaped punch to obtain tablets.

Dissolution Profile:

| S. No. | Time (hr) | % drug released Parameters: USP Apparatus I, 100 rpm, 0.1N HCl (0-2 Hrs) followed by pH 6.8 Phosphate Buffer |
|---|---|---|
| 1. | 1 | 0.6 |
| 2. | 2 | 1.7 |
| 3. | 3 | 39.8 |
| 4. | 4 | 61.5 |
| 5. | 6 | 84.2 |
| 6. | 8 | 92.8 |
| 7. | 10 | 95.9 |

Example-6

| S. No. | Ingredient | Quantity/tablet (mg) |
|---|---|---|
| 1. | Mycophenolate sodium (equivalent to 720 mg of mycophenolate sodium) | 773.5 |
| 2. | Lactose anhydrous | 120.5 |
| 3. | Hydroxypropyl methylcellulose (HPMC K100CR) | 180 |
| 4. | Ammonio methacrylate copolymer (Eudragit ® RSPO) | 60 |
| 5. | Acrylic and methacrylic ester copolymer (Eudragit ® RS30D) | 24 |
| 6. | 1N HCl solution | q.s. |
| 7. | Xanthan gum | 18 |
| 8. | Magnesium stearate | 24 |

Procedure:

i) Mycophenolate sodium, lactose anhydrous, HPMC K100CR, Eudragit® RSPO and xanthan gum were weighed, passed through mesh #40 sieve and mixed for 5 mins.

ii) Eudragit® RS30D was weighed and the pH was adjusted with 1N HCl solution to pH 2.0.

iii) The blend of step (i) was granulated using the dispersion of step (ii) and dried, passed through mesh #24 sieve to obtain the granules.

iv) Step (iii) granules were lubricated with mesh #40 passed magnesium stearate and compressed with caplet shaped punch to obtain tablets.

Dissolution Profile:

| S. No. | Time (hr) | USP Apparatus I, 100 rpm 0.1N HCl (0-2 Hrs) followed by pH 6.8 Phosphate Buffer % drug released | USP Apparatus II, 100 rpm |
| --- | --- | --- | --- |
| 1. | 1 | 0.6 | 1.6 |
| 2. | 2 | 1.1 | 2.7 |
| 3. | 3 | 13.0 | 16.0 |
| 4. | 4 | 19.7 | 35.1 |
| 5. | 6 | 33.6 | 49.7 |
| 6. | 8 | 42.5 | 63.9 |
| 7. | 10 | 52.7 | 75.1 |
| 8. | 12 | 60.3 | 87.8 |
| 9. | 14 | 68.8 | 97.4 |
| 10. | 16 | 74.0 | — |
| 11. | 20 | 93.3 | — |

Example-7

| S. No. Core composition | Ingredient | Quantity/ tablet (mg) |
| --- | --- | --- |
| 1. | Mycophenolate sodium (equivalent to 720 mg of mycophenolate sodium) | 773.5 |
| 2. | Lactose anhydrous | 46.5 |
| 3. | Carboxyvinyl polymer (Carbopol 71G) | 100 |
| 4. | Hydroxypropyl methylcellulose | 50 |
| 5. | Colloidal silicon dioxide | 5 |
| 6. | Talc | 5 |
| 7. | Magnesium stearate | 5 |
| 8. | Colloidal silicon dioxide | 5 |
| 9. | Talc | 5 |
| 10. | Magnesium stearate | 5 |

Procedure:

i) Mycophenolate sodium, lactose anhydrous, colloidal silicon dioxide and hydroxypropyl methylcellulose were weighed, sifted passed through mesh #40 sieve and mixed well for 5 mins.

ii) The powder of step (i) blend was lubricated with mesh #40 passed magnesium stearate, talc and colloidal silicon dioxide followed by slugging of the blend.

iii) The slugs were passed through mesh #24 sieve and retained with mesh #40 sieve to obtain granules.

iv) The granules of step (iii) were lubricated with mesh #40 passed magnesium stearate, talc and colloidal silicon dioxide and compressed with caplet shaped punch to obtain tablets.

Dissolution Profile:

| S. No. | Time (hr) | % drug released Parameters: USP Apparatus I, 100 rpm, DM Water |
| --- | --- | --- |
| 1. | 1 | 14.2 |
| 2. | 2 | 24.0 |
| 3. | 3 | 33.5 |
| 4. | 4 | 41.9 |
| 5. | 6 | 54.0 |
| 6. | 8 | 68.2 |
| 7. | 10 | 79.9 |
| 8. | 12 | 80.7 |
| 9. | 16 | 81.4 |
| 10. | 20 | 82.6 |
| 11. | 24 | 85.1 |

Example-8

| S. No. | Ingredient | Quantity/ tablet (mg) |
| --- | --- | --- |
| | Intra-granular addition | |
| 1. | Mycophenolate sodium (equivalent to 720 mg of mycophenolate sodium) | 773.5 |
| 2. | Lactose anhydrous | 36.5 |
| 3. | Glyceryl behenate (Compritol ® ATO888) | 27 |
| 4. | Colloidal silicon dioxide | 9 |
| | Granulating agent | |
| 5. | Ammonio methacrylate copolymer (Eudragit ® RSPO) | 45 |
| 6. | Dichloromethane:Isopropyl alcohol | 5 ml |
| | Extra-granular addition | |
| 7. | Magnesium stearate | 9 |

Procedure:

i) Mycophenolate sodium, lactose anhydrous, colloidal silicon dioxide and glyceryl behenate were weighed and passed through mesh #40 sieve and mixed for 5 mins.

ii) Ammonio methacrylate copolymer were weighed & dissolved in dichloromethane:isopropyl alcohol under stirring.

iii) The blend of step (i) was granulated using the solution of step (ii), dried and passed through suitable sieves to obtain granules.

iv) Step (iii) granules were lubricated with mesh #40 passed magnesium stearate and compressed to obtain tablets.

Dissolution Profile:

| S. No. | Time (hr) | % drug released Parameters: USP Apparatus I, 100 rpm, 0.1N HCl (0-2 Hrs) followed by pH 6.8 Phosphate Buffer |
| --- | --- | --- |
| 1. | 1 | 1.8 |
| 2. | 2 | 1.8 |
| 3. | 3 | 24.5 |
| 4. | 4 | 41.2 |
| 5. | 6 | 62.8 |
| 6. | 8 | 75.9 |
| 7. | 10 | 85.0 |
| 8. | 12 | 89.7 |
| 9. | 14 | 91.7 |
| 10. | 16 | 93.9 |
| 11. | 20 | 97.2 |

Example-9

| S. No. | Ingredient | Quantity/tablet (mg) |
|---|---|---|
| | Intra-granular addition | |
| 1. | Mycophenolate sodium (equivalent to 720 mg of mycophenolate sodium) | 773.5 |
| 2. | Lactose anhydrous | 36.5 |
| 3. | Glyceryl behenate (Compritol ® ATO888) | 27 |
| 4. | Colloidal silicon dioxide | 9 |
| | Granulating agent | |
| 5. | Ammonio methacrylate copolymer (Eudragit ® RSPO) | 45 |
| 6. | Dichloromethane:Isopropyl alcohol | 5 ml |
| | Extra-granular addition | |
| 7. | Magnesium stearate | 9 |
| | Coating composition | |
| 8. | Ammonio methacrylate copolymer (Eudragit ® RSPO) | 17.1 |
| 9. | Ammonio methacrylate copolymer (Eudragit ® RLPO) | 8.6 |
| 10. | Dibutyl sebacate | 6.4 |
| 11. | Talc | 12.9 |
| 12. | Dichloromethane:Isopropyl alcohol (1:3) | q.s. |

Procedure:
i) Mycophenolate sodium, lactose anhydrous, colloidal silicon dioxide and glyceryl behenate were weighed and passed through mesh #40 sieve and mixed for 5 mins.
ii) Ammonia methacrylate copolymer (Eudragit® RSPO) was weighed and dissolved in dichloromethane:isopropyl alcohol under.
iii) The blend of step (i) was granulated using the solution of step (ii), dried and passed through suitable sieves to obtain granules.
iv) Step (iii) granules were lubricated with mesh #40 sieve passed magnesium stearate and compressed to obtain tablets.

Coating Solution Preparation:
v) Ammonio methacrylate copolymer (Eudragit® RSPO) and ammonio methacrylate copolymer (Eudragit® RLPO) were dissolved in dichloromethane:isopropyl alcohol by continuous stirring.
vi) First dibutyl sebacate was added to solution of step (v) followed by dispersion of talc under continuous stirring.
vii) Finally the tablets were coated with the non-aqueous dispersion of step (vi).

Dissolution Profile:

| S. No. | Time (hr) | % drug released Parameters: USP Apparatus II, 100 rpm, 0.1N HCl (0-2 Hrs) followed by pH 6.8 Phosphate Buffer |
|---|---|---|
| 1. | 1 | 0.7 |
| 2. | 2 | 1.0 |
| 3. | 3 | 1.6 |
| 4. | 4 | 21.4 |
| 5. | 6 | 6.2 |
| 6. | 8 | 16.0 |
| 7. | 10 | 30.8 |
| 8. | 12 | 50.5 |
| 9. | 14 | 70.7 |
| 10. | 16 | 86.5 |
| 11. | 20 | 98.1 |

Example-10

| S. No. | Ingredient | Quantity/tablet (mg) |
|---|---|---|
| | Intra-granular addition | |
| 1. | Mycophenolate sodium (equivalent to 720 mg of mycophenolate sodium) | 773.5 |
| 2. | Lactose (Pharmatose DCL21) | 26.5 |
| 3. | Colloidal silicon dioxide | 5 |
| 4. | Polyvinyl pyrrolidone (PVP K-90) | 25 |
| 5. | Hydroxypropyl methylcellulose (HPMC K100 M CR) | 100 |
| 6. | Polyethylene oxide (Polyox WSR 301) | 50 |
| | Granulating agent | |
| 7. | Polyvinyl pyrrolidone (PVP K-30) | 10 |
| 8. | Isopropyl alcohol | 375 (ml) |
| | Extra-granular addition | |
| 9. | Magnesium stearate | 1 |

Procedure
i) Mycophenolate sodium, lactose, colloidal silicon dioxide, polyvinyl pyrrolidone (PVP K-90), polyethylene oxide (Polyox WSR 301) and hydroxypropyl methylcellulose (HPMC K100 M CR) were weighed and passed through mesh #40 sieve and mixed for 5 mins.
ii) Polyvinyl pyrollidone (PVP K-30) was weighed & dissolved in isopropyl alcohol under stirring.
iii) The blend of step (i) was granulated using the solution of step (ii), dried and passed through suitable sieves to obtain granules.
iv) Step (iii) granules were lubricated with mesh#40 passed magnesium stearate and compressed to obtain tablets.

Dissolution Profile:

| S. No. | Time (hr) | % drug released Parameters: USP Apparatus II, 100 rpm, DM water, 900 ml |
|---|---|---|
| 1. | 1 | 18.6 |
| 2. | 2 | 31.4 |
| 3. | 3 | 44.4 |
| 4. | 4 | 56.3 |
| 5. | 6 | 74.9 |
| 6. | 8 | 89.1 |
| 7. | 10 | 97.2 |

Example-11

| S. No. | Ingredient | Quantity/tablet (mg) |
|---|---|---|
| | Intra-granular addition | |
| 1. | Mycophenolate sodium | 500 |
| 2. | Lactose anhydrous | 107.75 |
| 3. | Hydroxypropyl methylcellulose (HPMC K100 M CR) | 127.5 |
| 4. | Sodium alginate | 85 |
| | Granulating agent | |
| 5. | Polyvinyl pyrrolidone (PVP K-30) | 21.25 |
| 6. | Isopropyl alcohol | 3.25 (ml) |
| | Extra-granular addition | |
| 7. | Magnesium stearate | 0.85 |

Procedure i) Mycophenolate sodium, lactose anhydrous, sodium alginate and hydroxypropyl methylcellulose (HPMC K100 M CR) were weighed and passed through mesh #40 sieve and mixed for 5 mins.

ii) Polyvinyl pyrollidone (PVP K-30) was weighed & dissolved in isopropyl alcohol under stirring.

iii) The blend of step (i) was granulated using the solution of step (ii), dried and passed through suitable sieves to obtain granules.

iv) Step (iii) granules were lubricated with mesh#40 passed magnesium stearate and compressed to obtain tablets.

The invention claimed is:

1. A composition comprising:
    (a) mycophenolate sodium in an amount equivalent to about 720 mg of mycophenolate sodium;
    (b) hydroxypropyl methylcellulose in an amount of about 183 mg;
    (c) polyethylene oxide in an amount of about 26 mg; and
    (d) polyvinyl pyrrolidone in an amount of about 36 mg.

2. A composition comprising:
    (a) mycophenolate sodium in an amount equivalent to about 720 mg of mycophenolate sodium;
    (b) hydroxypropyl methylcellulose in an amount of about 100 mg;
    (c) polyethylene oxide in an amount of about 50 mg.

* * * * *